United States Patent [19]

Soula et al.

[11] 4,417,048

[45] Nov. 22, 1983

[54] N-ALKYLATION OF ORGANONITROGEN COMPOUNDS

[75] Inventors: Gerard Soula, Meyzieu; Maurice Balme, Saint Foy les Lyon, France

[73] Assignee: Rhone-Poulenc Specialties Chimiques, Courbevoie, France

[21] Appl. No.: 351,867

[22] Filed: Feb. 24, 1982

[30] Foreign Application Priority Data

Mar. 11, 1981 [FR] France ............................... 81 04823

[51] Int. Cl.$^3$ ........................................... C07D 279/22
[52] U.S. Cl. ..................................... 544/38; 548/473; 548/445; 548/446; 548/257; 548/373; 548/325; 548/335; 548/469; 548/564; 564/305; 564/441; 260/465 E
[58] Field of Search ............... 548/473, 445, 446, 257, 548/373, 325, 335, 469, 564; 544/38; 564/305, 441; 260/465 E

[56] References Cited

U.S. PATENT DOCUMENTS

| | | | |
|---|---|---|---|
| 3,002,976 | 10/1961 | Janssen | 544/379 |
| 3,097,206 | 7/1963 | Zirkle | 544/379 |
| 3,773,759 | 11/1973 | Cusic et al. | 544/376 |
| 3,917,634 | 11/1975 | Houlihan | 548/346 |
| 3,933,860 | 1/1976 | Chan | 549/321 |
| 4,105,670 | 8/1978 | Noguchi et al. | 548/411 |

OTHER PUBLICATIONS

Guida et al., J. Org. Chem. 1980, 45, 3172–3176.
Masse, Synthesis, p. 342, (1977).
Jones, J. Chem. Soc., (c), 1971, p. 132.

Primary Examiner—Jane T. Fan
Attorney, Agent, or Firm—Burns, Doane, Swecker & Mathis

[57] ABSTRACT

Organonitrogen compounds bearing a labile hydrogen atom directly bonded to a reactive nitrogen function, e.g., nitrogen heterocycles or substituted anilines, are N-alkylated with an N-alkylating agent in the presence of inorganic base and at least one sequestering agent having the structural formula:

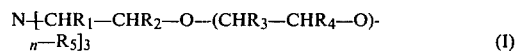

$$N{+}[CHR_1{-}CHR_2{-}O{-}(CHR_3{-}CHR_4{-}O)_n{-}R_5]_3 \qquad (I)$$

wherein n is a number ranging from 0 to 10, $R_1$, $R_2$, $R_3$, $R_4$, which may be identical or different, each represents a hydrogen atom or an alkyl radical having 1 to 4 carbon atoms, and $R_5$ represents an alkyl or cycloalkyl radical having 1 to 12 carbon atoms, a phenyl radical, or a radical of the formula $-C_mH_{2m}-\phi$, or $C_mH_{2m+1}-\phi-$, m ranging from 1 to about 12 and $\phi$ being phenyl.

17 Claims, No Drawings

N-ALKYLATION OF ORGANONITROGEN COMPOUNDS

BACKGROUND OF THE INVENTION

1. Field of the Invention

The present invention relates to the N-alkylation of organic nitrogen compounds, and, more especially, to such N-alkylation by reacting an organic compound comprising a nitrogen atom to which a labile hydrogen atom is directly bonded, with an alkylating agent, in the conjoint presence of a inorganic base and a certain tertiary amine sequestering agent.

2. Description of the Prior Art

The N-alkylation of organic nitrogen compounds is of course generally well known to this art.

Thus, in D. H. Jones, *J. Chem. Soc.* (c), 132 (1971), there is featured the reaction of substituted phenothiazines with substituted alkyl halides, such as 3-(N,N-dimethylamino)chloropropane, in dimethylformamide and in the presence of sodium hydride. The principal disadvantage of this type of process is its requirement for an aprotic polar solvent, the difficulties attendant the industrial scale application thereof also being well known to those skilled in the art. Furthermore, sodium hydride is an expensive and dangerous compound.

The same reaction has been catalytically carried out by liquid/liquid phase transfer. Such method, described in J. Masse, *Synthesis*, p. 342 (1977) employs a two-phase water/benzene system in the presence of a quaternary ammonium to alkylate 2-chlorophenothiazine. Results obtained utilizing chlorinated alkylating agents [$C_6H_5$—$CH_2$—Cl, $(H_3C)_2N$—$(CH_2)_3$—Cl] were negative (yields of 0 to 20%), albeit those results obtained with brominated alkylating agents [$H_2C$=CH—$CH_2$—Br, $C_2H_5Br$, Cl—$(CH_2)_3Br$], which are more reactive, were better (on the order of 40–55%), but were not completely satisfactory on an industrial scale.

The same liquid/liquid phase transfer method was utilized by H. J.-M. Dou and J. Metzger, who describe the N-alkylation of certain heterocyclic compounds, such as pyrazole and imidazole, with various alkylating agents. Only reactive alkylating agents, such as 1-bromobutane, 1-bromo-3-phenoxypropane and benzyl chloride, afford good yields (70–80%). Non-reactive alkylating agents, such as 1-chlorooctane, tertiary-butyl bromide, and dodecyl bromide provide negligible yields (on the order of 0 to 5%).

Compare also the article, C. Guida and David J. Mathre, *J. Org. Chem.*, 45, 3172 (1980), which features the N-alkylation of heterocyclic nitrogen compounds containing a labile hydrogen atom bonded to the nitrogen atom. The process described is a phase transfer process by which the substrate and the alkylating agent are reacted in diethyl ether in the presence of a base and a crown ether ("18-Crown-6"). The article notes only reactive alkylating agents such as methyl iodide, methyl bromide, ethyl iodide, and allyl bromide. It will be appreciated that this process is only difficultly applied on an industrial scale, by reason of the fact that the crown ethers are indeed economically problematical, a factor indeed limiting their use where economics are significant.

It is thus seen that there exists serious need in this art for a process for the N-alkylation of nitrogen compounds, which, on the one hand, does not require the use of solvents and reagents, the industrial handling of which is delicate, and, on the other, permits the utilization of mildly reactive alkylating agents, the latter being generally more readily available.

SUMMARY OF THE INVENTION

Accordingly, a major object of the present invention is the provision of an improved process for the N-alkylation of organic nitrogen compounds which avoids those aforementioned disadvantages and drawbacks, and which is characterized in that the organic nitrogen compound starting materials comprising a labile hydrogen atom bonded to the nitrogen function is reacted with an alkylating agent in the presence, on the one hand, of an base and, on the other, at least one sequestering agent having the structural formula (I):

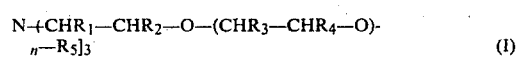

$$N + CHR_1 - CHR_2 - O - (CHR_3 - CHR_4 - O) - {}_n - R_5]_3 \quad (I)$$

wherein n is an integer greater than or equal to 0 and less than or equal to approximately 10 ($0 \leq n \leq 10$), $R_1$, $R_2$, $R_3$, $R_4$, which may be identical or different, each represents a hydrogen atom or an alkyl radical having 1 to 4 carbon atoms, and $R_5$ represents an alkyl or cycloalkyl radical having 1 to 12 carbon atoms, a phenyl radical, or a radical of the formula —$C_mH_{2m}$—$\phi$, or $C_mH_{2m+1}$—$\phi$—, m ranging from 1 to about 12 and $\phi$ being phenyl.

DETAILED DESCRIPTION OF THE INVENTION

More particularly according to the present invention, the starting material nitrogen compounds are advantageously heterocyclic nitrogen compounds, or substituted aniline compounds having the structural formula:

wherein A is in the ortho- and/or para-position and represents at least one electron accepting group imparting to the hydrogen atom directly bonded to the nitrogen atom a sufficiently acid character as to enable the reaction to proceed.

The following are representative examples of such starting material nitrogen compounds: para-nitroaniline, ortho-nitroaniline, para-cyanoaniline, ortho-cyanoaniline, ortho-trifluoromethylaniline, para-trifluoromethylaniline, and 2,4-dinitroaniline.

And exemplary of the heterocyclic nitrogen compound starting materials are pyrole, indole, pyrazole, imidazole, benzimidazole, benzotriazole, carbazole, phenothiazine, phthalimide, and derivatives thereof.

N-alkylating agents which are conveniently utilized consistent herewith have the following general formula:

$$R_6 - (X) \quad (III)$$

wherein $R_6$ is an optionally substituted alkyl radical having 1 to 12 carbon atoms, an optionally substituted benzyl radical, or an optionally substituted allyl radical, said optional substituents comprising any moiety that is unreactive under the conditions of the N-alkylation reaction, and X is Cl, Br, I, alkylsulfonate or arylsulfonate.

The most preferred N-alkylating agents are those wherein X is a chlorine atom.

The following are representative such alkylating agents: chloroalkanes, such as methyl chloride, ethyl chloride, isopropyl chloride, hexyl chloride, chlorooctane, 3-(N,N-dimethylamino)chloropropane, 1,2-dichloroethane, benzyl chloride, para-chlorotoluene, allyl chloride, methallyl chloride. The corresponding bromide compounds are also exemplary; their use, however, is generally of less interest.

The inorganic base employed in the process of the invention is preferably selected from among the hydroxides, bicarbonates and the carbonates of the alkali and alkaline earth metals. Exemplary of such preferred bases are sodium hydroxide, lithium hydroxide, potassium hydroxide, sodium bicarbonate, sodium carbonate, potassium carbonate and lime.

In a preferred embodiment of the invention, in the art least one tertiary amine sequestering agent having the Formula (I), $R_1$, $R_2$, $R_3$ and $R_4$ are preferably hydrogen or methyl, and $R_5$ and n are as above defined.

Even more preferably among such preferred sequestering agents, n is greater than or equal to 0 and less than or equal to 6, and $R_5$ is an alkyl radical having 1 to 4 carbon atoms.

Exemplary of such preferred sequestering agents are:
(1) Tris(3-oxabutyl)amine having the formula:

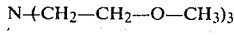

(2) Tris(3-oxaheptyl)amine having the formula:

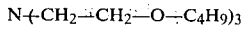

(3) Tris(3,6-dioxaheptyl)amine having the formula:

N+CH$_2$—CH$_2$—O—CH$_2$—CH$_2$—O—CH$_3$)$_3$ (4) Tris(3,6,9-trioxadecyl)amine having the formula:

N+CH$_2$—CH$_2$—O—CH$_2$—CH$_2$—O—CH$_2$—CH$_2$—O—CH$_3$)$_3$ (5) Tris(3,6-dioxaoctyl)amine having the formula:

N+CH$_2$—CH$_2$—O—CH$_2$—CH$_2$—O—C$_2$H$_5$)$_3$ (6) Tris(3,6,9-trioxaundecyl)amine having the formula:

N+CH$_2$—CH$_2$—O—CH$_2$—CH$_2$—O—CH$_2$—CH$_2$—O—C$_2$H$_5$)$_3$ (7) Tris(3,6-dioxanonyl)amine having the formula:

N+CH$_2$—CH$_2$—O—CH$_2$—CH$_2$—O—C$_3$H$_7$)$_3$ (8) Tris(3,6,9-trioxadodecyl)amine having the formula:

N+CH$_2$—CH$_2$—O—CH$_2$—CH$_2$—O—CH$_2$—CH$_2$—O—C$_3$H$_7$)$_3$ (9) Tris(3,6-dioxadecyl)amine having the formula:

N+CH$_2$—CH$_2$—O—CH$_2$—CH$_2$—O—C$_4$H$_9$)$_3$

(10) Tris(3,6,9-trioxatridecyl)amine having the formula:

N+CH$_2$—CH$_2$—O—CH$_2$—CH$_2$—O—CH$_2$—CH$_2$—O—C$_4$H$_9$)$_3$

(11) Tris(3,6,9,12-tetraoxatridecyl)amine having the formula:

N+CH$_2$—CH$_2$—O+CH$_2$—CH$_2$+O)$_3$CH$_3$]$_3$

(12) Tris(3,6-dioxa-4-methylheptyl)amine having the formula:

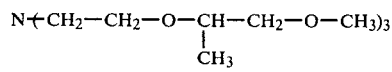

and (13) Tris(3,6-dioxa-2,4-dimethylheptyl)amine having the formula:

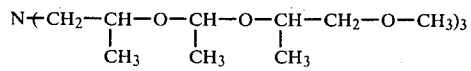

The sequestering agents employed in the process according to this invention are conveniently prepared via that procedure outlined in French Patent Application No. 79-05438, published under No. 2,450,120.

The process according to the invention may also be carried out either in the presence or absence of a reaction solvent. When such a solvent is indeed employed, same is preferably an aprotic, apolar solvent, or an aprotic solvent of low polarity, such as, for example, benzene, toluene, chlorobenzene, dichlorobenzene, dichloromethane and acetonitrile.

It too is envisaged to conduct the reaction in the absence of any solvent; in this case the alkylating agent itself serves as the solvent.

It is preferred to use a solvent, however, if the alkylating agent employed is a compound that is either difficult to obtain and/or is expensive; the same is true if the alkylating agent is highly reactive (in this case, it is preferred to dilute same with the solvent).

Consistent herewith, the organic nitrogen compound and the alkylating agent are preferably used in amounts such that the molar ratio of the nitrogen compound to the alkylating agent ranges from about 0.1 to about 5. The high values constituting this ratio correspond to the instance when the alkylating agent is itself employed as the solvent.

The molar ratio of the sequestering agent to the organic nitrogen compound preferably ranges from about 0.01 to about 0.1. Even more preferably, this ratio ranges from about 0.02 to about 0.08.

In another preferred embodiment of the invention, the base is used in amounts such that the molar ratio of the inorganic base to the organic nitrogen compound ranges from about 1 to about 5, and more preferably ranges from about 1 to about 2.

The process according to the invention is preferably carried out at a temperature ranging from about 0° C. to about 200° C., at atmospheric pressure. Pressures greater or less than atmospheric nonetheless remain within the ambit of the invention.

The compounds prepared according to the process of the invention correspond to the beginning organic nitrogen compounds, but containing instead and in the position of the labile hydrogen atom directly bonded to the nitrogen atom, the radical $R_6$ emanating from the alkylating agent. Such final products are useful intermediates in the synthesis of numerous organic compounds.

In order to further illustrate the present invention and the advantages thereof, the following specific examples are given, it being understood that same are intended only as illustrative and in nowise limitative.

EXAMPLE 1

N-Alkylation of Phthalimide

Into a 150 ml reactor equipped with a magnetic agitator, a condenser and a thermometer, the following materials were successively introduced: 20 cm$^3$ acetonitrile, 0.025 mole phthalimide (3.67 g), 0.025 mole potassium carbonate (3.45 g), 0.025 mole bromodecane (5.5 g) and 0.001 mole tris(3,6-dioxaheptyl)amine (0.32 g).

The reaction was heated under reflux and under agitation for 6 hours, then cooled and analyzed by means of gaseous phase chromatography.

With reference to appropriate standards, the yield of the reaction was determined: same was equal to 93%.

COMPARATIVE EXAMPLE 1

Example 1 was repeated, but in the absence of the tris(3,6-dioxaheptyl)amine, everything else being equal; the reaction yield was 42%.

EXAMPLE 2

N-Alkylation of Phthalimide

The procedure of Example 1 was repeated, but the acetonitrile was replaced with chlorobenzene. After 8 hours at reflux, the reaction yield was 70%.

COMPARATIVE EXAMPLE 2

Example 2 was repeated, but without the catalyst; the reaction yield was 0%.

EXAMPLE 3

N-Alkylation of Benzimidazole

Into a 150 ml reactor equipped with a magnetic agitator, a condenser and thermometer, the following materials were successively introduced: 20 cm$^3$ toluene, 0.02 mole of chlorooctane (2.97 g), 0.02 mole of potash, 0.02 mole of benzimidazole (2.36 g) and 0.002 mole of tris(3,6-dioxaheptyl)amine (0.64 g). The reaction mixture was heated under reflux and under agitation for 5 hours, then cooled and analyzed by gaseous phase chromatography. With reference to appropriate standards, the yield of the reaction was determined; same was equal to 76%.

COMPARATIVE EXAMPLE 3

Repeating Example 3, but in the absence of the tris(3,6-dioxaheptyl)amine, the reaction yield was 10%.

EXAMPLE 4

N-Alkylation of Pyrole

Into the reactor described in Example 1, the following materials were successively introduced: 20 cm$^3$ toluene, 0.01 mole of pyrole (0.67 g), 0.01 mole of potash (0.65 g), 0.01 mole of bromohexane (1.65 g) and 0.16 g tris(3,6-dioxaoctyl)amine (0.0005 mole). After 4 hours of heating at reflux, the reaction yield was determined by chromatographic analysis in gaseous phase to be 95%.

COMPARATIVE EXAMPLE 4

Repeating Example 4, but without the catalyst, and otherwise under the same conditions, the reaction yield was 0%.

EXAMPLE 5

N-Alkylation of Para-Nitroaniline

Into a 100 ml reactor equipped with a magnetic agitator and a reflux condenser, the following materials were successively introduced: 20 cm$^3$ anhydrous toluene, 1.31 g potash (0.02 mole), 3,3 g bromohexane (0.02 mole), 2.76 g para-nitroanaline (0.02 mole) and 0.32 g tris(3,6-dioxaheptyl)amine (10$^3$ mole). The reaction mixture was heated under reflux for one hour, then cooled and washed with 20 cm$^3$ water; the organic phase was recovered, dried and the toluene distilled. By means of infra red and mass spectrometry, N-hexyl para-nitroaniline was identified. The yield of the reaction was 86%.

COMPARATIVE EXAMPLE 5

The procedure of Example 5 was repeated, under the same conditions, but in the absence of the tris(3,6-dioxaheptyl)-amine; the reaction did not take place.

EXAMPLE 6

N-Alkylation of 2-Chlorophenothiazine

The following materials were introduced into a 125 ml reactor: 4.07 g 2-chlorophenothiazine (0.01743 mole), 0.785 g sodium hydroxide in tablet form having a purity of 97.7% (0.0192 mole, finely ground: in 10% excess), 0.630 g tris(3,6-dioxaoctyl)amine (0.00175 mole) and 65 ml toluene.

The reactor was immersed in a bed thermostated at 100° C. When the reaction mass was at reflux, the following materials were introduced thereto over the course of 2 hours: 2.60 g 3-dimethylamino-2-methyl-1-chloropropane, in a 578 g/l solution in toluene. Three hours after the completion of the addition of the 3-dimethylamino-2-methyl-1-chloropropane, the reaction mass was cooled and poured into water. The organic phase was decanted and washed in water.

Gas chromatography evidenced that 0.0103 mole of the 2-chlorophenothiazine derivative having the following structural formula had been formed.

The amount converted was 65% and the reaction yield was 59%.

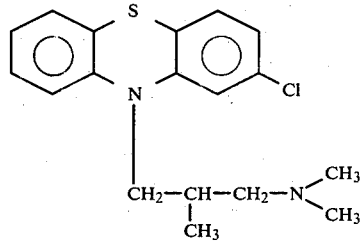

COMPARATIVE EXAMPLE 6

The procedure of Example 6 was repeated, under the same conditions, but without the tris(3,6-dioxaoctyl)amine and with the following reagents: 4.56 g 2-chlorophenothiazine, 0.888 g powdered sodium hydroxide having a purity of 97.8% (0.0217 mole), 5.1 ml 3-dimethylamino-2-methyl-1-chloropropane in a 578 g/l toluene solution.

The toluene solution of 3-dimethylamino-2-methyl-1-chloropropane was introduced with reflux over 2 hours, 10 min, and the reaction was permitted to proceed for 3 hours under reflux.

The degree of conversion was 13%.

EXAMPLE 7

N-Alkylation of 2-Chlorophenothiazine

The procedure of Example 6 was repeated, but by replacing the sodium hydroxide with an equal molar amount of potash (purity: 86.8%).

The amount converted was 98% and the yield was 94%.

COMPARATIVE EXAMPLE 7

Comparative Example 6 was repeated, but with the sodium hydroxide being replaced with an equal molar amount of potash (86.8% purity).

The degree of conversion was 89% and the yield was 86%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a process for the N-alkylation of an organonitrogen compound, comprising N-alkylating an organonitrogen compound bearing a labile hydrogen atom directly bonded to the nitrogen atom to be N-alkylated, with an N-alkylating agent, in the presence of an inorganic base, the improvement comprising conducting said N-alkylation in the presence of a sequestering agent having the structural formula:

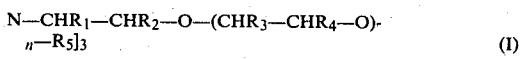

wherein n is a number ranging from 0 to about 10, $R_1$, $R_2$, $R_3$, $R_4$, which may be identical or different, each represents a hydrogen atom or an alkyl radical having 1 to 4 carbon atoms, and $R_5$ represents an alkyl or cycloalkyl radical having 1 to 12 carbon atoms, a phenyl radical, or a radical of the formula $-C_mH_{2m}-\phi$, or $C_mH_{2m+1}-\phi-$, m ranging from 1 to about 12 and $\phi$ being phenyl.

2. The process as defined by claim 1, wherein the sequestering agent having the structural formula (I), $R_1$, $R_2$, $R_3$ and $R_4$ are each hydrogen or methyl.

3. The process as defined by claim 2, wherein the sequestering agent having the structural formula (I), n ranges from 0 to 6, and $R_5$ is an alkyl radical having from 1 to 4 carbon atoms.

4. The process as defined by claim 1, said organonitrogen compound starting material being a nitrogen heterocycle or a substituted aniline having the structural formula:

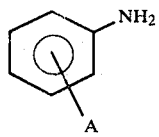

wherein A is in the ortho- and/or para-position and is an electron accepting group.

5. The process as defined by claim 4, said organonitrogen compound starting material being pyrole, indole, pyrazole, imidazole, benzimidazole, benzotriazole, carbazole, phenothiazine or phthalimide.

6. The process as defined by claim 4, said organonitrogen compound starting material being para-nitroaniline, ortho-nitroaniline, para-cyanoaniline, ortho-cyanoaniline, ortho-trifluoromethylaniline, para-trifluoromethylaniline or 2,4-dinitroaniline.

7. The process as defined by claims 1 or 4, said N-alkylating agent having the structural formula:

wherein $R_6$ is an optionally substituted alkyl radical having 1 to 12 carbon atoms, an optionally substituted benzyl radical, or an optionally substituted allyl radical, said optional substituents comprising any moiety that is unreactive under the conditions of the N-alkylation reaction, and X is Cl, Br, I, alkylsulfonate or arylsulfonate.

8. The process as defined by claim 7, wherein the N-alkylating agent having the structural formula (III), X is Cl.

9. The process as defined by claim 7, said inorganic base being an hydroxide, bicarbonate or carbonate of an alkali or alkaline earth metal.

10. The process as defined by claim 9, said inorganic base being sodium hydroxide, lithium hydroxide, potassium hydroxide, sodium bicarbonate, sodium carbonate, potassium carbonate or lime.

11. The process as defined by claim 7, said N-alkylating agent being methyl chloride, ethyl chloride, isopropyl chloride, hexyl chloride, chlorooctane, 3-(N,N-dimethylamino)chloropropane, 1,2-dichloroethane, benzyl chloride, para-chlorotoluene, allyl chloride, methallyl chloride, or bromide analog thereof.

12. The process as defined by claim 7, said N-alkylation being carried out in an inert reaction solvent.

13. The process as defined by claim 12, said solvent being an apolar or slightly polar aprotic solvent.

14. The process as defined by claim 7, wherein the molar ratio of the organonitrogen compound starting material to the N-alkylating agent ranges from about 0.1 to about 5.

15. The process as defined by claim 14, wherein the molar ratio of the sequestering agent to the organonitrogen compound ranges from about 0.01 to about 0.1.

16. The process as defined by claim 15, wherein the molar ratio of the base to the organonitrogen compound ranges from about 1 to about 5.

17. The process as defined by claim 7, said sequestering agent being tris(3-oxabutyl)amine, tris(3-oxaheptyl)amine, tris(3,6-dioxaheptyl)amine, tris(3,6,9-trioxadecyl)amine, tris(3,6-dioxaoctyl)amine, tris(3,6,9-trioxaundecyl)amine, tris(3,6-dioxanonyl)amine, tris(3,6,9-trioxadodecyl)amine, tris(3,6-dioxadecyl)amine, tris(3,6,9-trioxatridecyl)amine, tris(3,6,9,12-tetraoxatridecyl)-amine, tris(3,6-dioxa-4-methylheptyl)amine, or tris(3,6-dioxa-2,4-dimethylheptyl)amine.

* * * * *